(12) United States Patent
Nakamura

(10) Patent No.: US 8,758,309 B2
(45) Date of Patent: Jun. 24, 2014

(54) GAS MIST MASK DEVICE

(75) Inventor: Shoichi Nakamura, Higashichikuma-gun (JP)

(73) Assignees: ACP Japan Co., Ltd., Tokyo (JP); Shoichi Nakamura, Higashichikuma-gun, Nagano (JP)

( * ) Notice: Subject to any disclaimer, the term of this patent is extended or adjusted under 35 U.S.C. 154(b) by 71 days.

(21) Appl. No.: 13/138,588

(22) PCT Filed: Jun. 12, 2010

(86) PCT No.: PCT/JP2010/059982
§ 371 (c)(1),
(2), (4) Date: Sep. 8, 2011

(87) PCT Pub. No.: WO2011/013450
PCT Pub. Date: Feb. 3, 2011

(65) Prior Publication Data
US 2012/0004599 A1    Jan. 5, 2012

(30) Foreign Application Priority Data

Jul. 29, 2009  (JP) ................................ 2009-176960
Jul. 29, 2009  (JP) ................................ 2009-176961

(51) Int. Cl.
*A61M 35/00* (2006.01)
*A61H 33/04* (2006.01)
*A61F 13/00* (2006.01)
*A61H 33/14* (2006.01)

(52) U.S. Cl.
CPC .......... *A61M 35/00* (2013.01); *A61H 2033/145* (2013.01); *A61F 13/00* (2013.01)
USPC .............................. 604/289; 604/303; 604/305

(58) Field of Classification Search
CPC ................ A61H 2203/145; A61H 2201/0207; A61H 2201/025; A61H 2205/06; A61H 2205/10; A61H 33/14; A61H 35/00; A61M 35/00; A61M 1/0088; A61M 1/0084; A61M 2205/3344; A61F 2013/00174; A61F 13/00; A61F 15/008

USPC .......................................... 604/289, 303, 305
See application file for complete search history.

(56) References Cited

U.S. PATENT DOCUMENTS 3,249,108 A * 5/1966 Terman .................... 128/204.17
4,792,097 A * 12/1988 Kremer et al. ................ 239/338
(Continued)

FOREIGN PATENT DOCUMENTS

JP   2004-073828   3/2004
JP   2006-055358   3/2006
(Continued)

*Primary Examiner* — Tatyana Zalukaeva
*Assistant Examiner* — Andrew J Mensh
(74) *Attorney, Agent, or Firm* — Manabu Kanesaka

(57) ABSTRACT

The present invention is to provide a gas mist mask device which is compact and economical, and enables to take a mist bath for the face or the eyes by using the physiological actions of oxygen or carbon dioxide. The gas mist mask device comprises a gas supply means 110 of supplying carbon or carbon dioxide, otherwise the mixed gas (called briefly as "gas" hereafter) of oxygen and carbon dioxide, a gas mist generating means 120 connected to the gas supply means for storing a liquid inside thereof and generating a mist (called as "gas mist" hereafter) prepared by pulverizing and dissolving the stored liquid and the gas, and a mask member having a mask main frame 131 with a first sheet passing the gas mist and a second sheet not passing, and holding parts 138 of securing the mask main frame 131 in such a manner that the first sheet is fronted to the eyes or the face of the human living organism, and this gas mist generating means supplies the gas mist between the first sheet and the second sheet, thereby contacting the gas mist to the eyes or the face of the human living organism.

16 Claims, 15 Drawing Sheets

(56) References Cited

U.S. PATENT DOCUMENTS

| | | | |
|---|---|---|---|
| 7,603,723 B2 * | 10/2009 | Ulm | 2/15 |
| 7,734,158 B2 * | 6/2010 | Kondo et al. | 392/325 |
| 2004/0243026 A1 * | 12/2004 | Toepfer et al. | 601/15 |
| 2004/0244792 A1 * | 12/2004 | Hashiba | 128/200.21 |
| 2005/0268910 A1 * | 12/2005 | Nord et al. | 128/204.14 |
| 2008/0021373 A1 * | 1/2008 | Rosati | 604/22 |
| 2008/0119800 A1 * | 5/2008 | Goldman et al. | 604/303 |
| 2010/0288562 A1 * | 11/2010 | Dove et al. | 175/340 |

FOREIGN PATENT DOCUMENTS

| | | |
|---|---|---|
| JP | 2007-181720 | 7/2007 |
| JP | U 3144717 | 8/2008 |
| JP | 2009-011695 | 1/2009 |
| JP | 2009-018136 | 1/2009 |

* cited by examiner

FIG.6
(a)
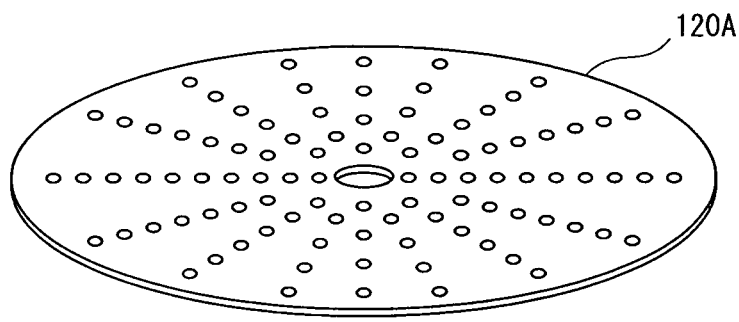
(b)
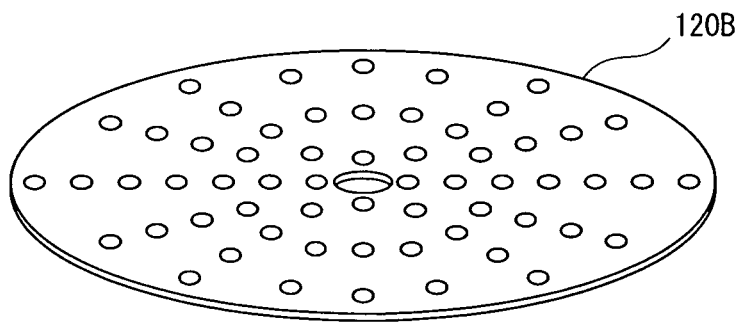

FIG.8
(a)
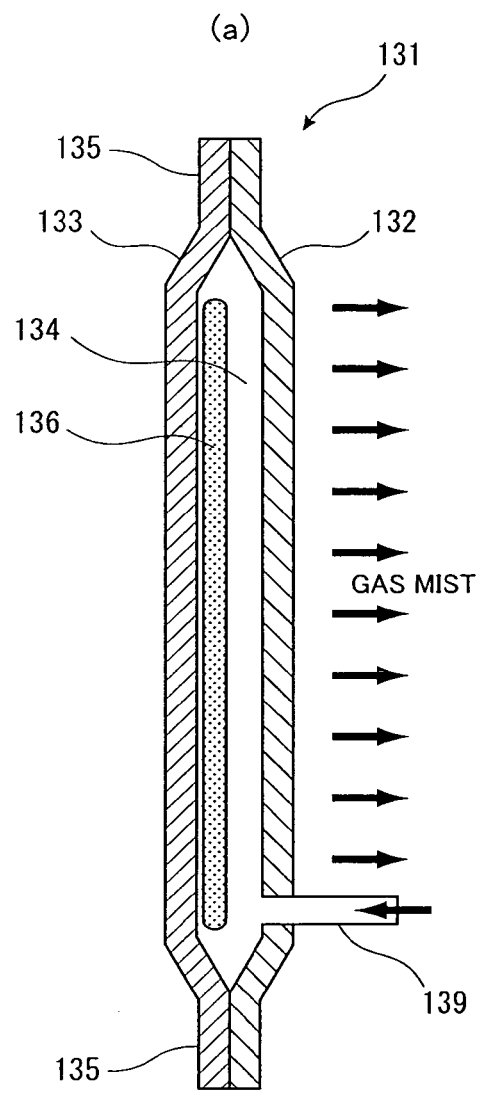
(b)
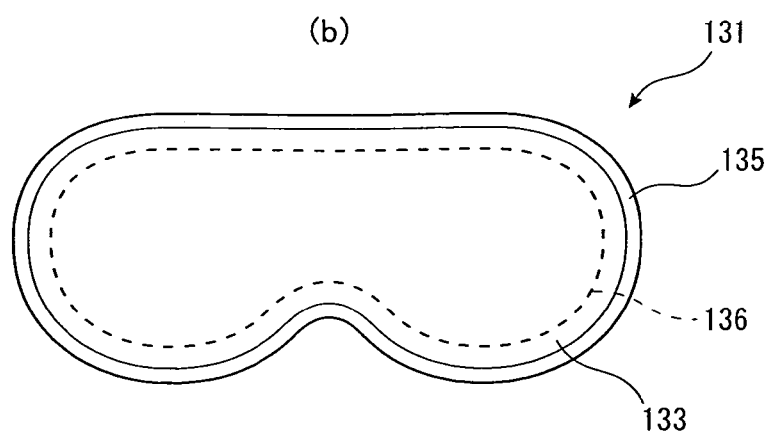

GAS MIST MASK DEVICE

RELATED APPLICATIONS

The present application is National Phase of International Application No. PCT/JP2010/059982 filed Jun. 12, 2010, and claims priorities from Japanese Application No. 2009-176960 filed Jul. 29, 2009 and No. 2009-176961 filed Jul. 29, 2009.

TECHNICAL FIELD

The present invention relates to a gas mist mask device for causing a gas mist to contact the face and eyes of a human living organism, which is prepared by pulverizing and solving oxygen, carbon dioxide, otherwise the mixed gas of oxygen and carbon dioxide, and liquid.

BACKGROUND ART

In recent years, by prevailing of air cooling and heating conditioners and increasing of heat insulated and airtight buildings, drying of indoor circumstances has advanced. Such drying has given various influences to a skin or mucous membrane, and caused skin troubles as wrinkles or itching, fatigue of the eyes or dry eye. For protecting the face and eyes of the human living organism from the drying, a mist bath (steam bath) is useful, giving moderate moisture and bathing effects to diseased parts.

By the way, it has conventionally been known that carbon dioxide (carbonic acid anhydride: $CO_2$) has both properties of being not only soluble in water (water-soluble) but also soluble in fat (fat-soluble) and, therefore, by only contacting the skin and mucous membrane of the living organism as being mixed with water and fat, carbon dioxide penetrates under a subcutaneous layer and expands blood vessels around the parts of penetrated carbon dioxide, and it works to improve the blood circulation. Owing to this action of accelerating the blood circulation, it displays various physiological effects such as dropping of blood pressure, improving of metabolism or accelerating to remove pain substance or waste product. Further, it has also anti-inflammation and anti-bacterial. Therefore, carbon dioxide has recently been given attentions also from viewpoints of improving health or beauty other than the purpose of medical cares.

Carbon dioxide in the tissue of the living organism works to release oxygen having been carried in combination with hemoglobin in a red blood cell. Around parts at a high density of carbon dioxide, the red blood cell releases more oxygen. Thus, supply of oxygen to cells by the red blood cell is mainly controlled by carbon dioxide. In short, being without carbon dioxide, hemoglobin remains as having been combined with oxygen and the cell becomes unable to receive oxygen. As is seen, carbon dioxide seems to be waste products resulted from action of the cell, however, it plays in fact very important roles in the living organism.

Further, recently, oxygen of the high density has also widely been known as effective in activity of metabolism, acceleration of blood circulation, fatigue recovery, or stability of blood pressure. Other than them, oxygen has effects of disinfection or sterilization by oxidation.

SUMMARY OF INVENTION

Problems to be Solved by the Invention

As having above mentioned, for protecting the face and eyes of the human living organism from drying or chilling, the mist bathing is useful, but for taking an effective mist bath for a time of a certain period, an exclusively using device is necessary to generate a mist applying to the face or the eyes. But many of such devices have been large scaled and expensive.

Besides, there has never been such a mist bathing device which dissolves oxygen or carbon dioxide in various kinds of medicines and can influence physiological actions of oxygen or carbon dioxide to the living organism in addition to the effects of these medicines.

Therefore, in view of the above mentioned situations, it is an object of the invention to provide a gas mist mask device which is compact and economical, and enables to take a mist bath for the face or the eyes by using the physiological actions of oxygen or carbon dioxide.

Means for Solving the Problem

For solving the problem, the present invention is to provide a gas mist mask device, which comprises a gas supply means of supplying carbon or carbon dioxide, otherwise the mixed gas (called briefly as "gas" hereafter) of oxygen and carbon dioxide, a gas mist generating means connected to the gas supply means for storing a liquid inside thereof and generating a mist (called as "gas mist" hereafter) prepared by pulverizing and dissolving the stored liquid and the gas, and a mask member having a mask main frame with a first sheet passing the gas mist and a second sheet not passing it, and holding parts of securing the mask main frame in such a manner that the first sheet is fronted to the eyes or the face of the human living organism, characterized in that the gas mist generating means supplies the gas mist between the first sheet and the second sheet, thereby contacting the gas mist to the eyes or the face of the human living organism.

By the way, the invention refers it as "pulverizing and dissolving" to pulverize the liquid into fine liquid drops, and cause to contact and mix with gas (oxygen, carbon dioxide, otherwise the mixed gas of oxygen and carbon dioxide).

Herein, the mask member is suitable to have a shape of an eye mask or a face mask.

In addition, the gas supply means is suitable to have a gas bomb of a cartridge system. Otherwise, the gas supply means may have any one or a plurality of a gas supplying time setting part, a gas supplying pressure adjusting part, and a gas mixing ratio setting part.

The gas mist generating means may be a type of supplying the gas mist into the plural mask members.

The above mentioned liquids are desirable to be any one or plural combination of water, ionic water, ozone water, physiological salt solution, purified water or sterilized and purified water, and those are preferable to contain anyone or plural combination of menthol, vitamin E, vitamin C derivative, retinol, anesthetic, cyclodextrin, photocatalyst, complex of photocatalyst and apatite, hyaluronic acid, coenzyme Q10, seed oil, propolith, silica, povidone-iodine, anti-allergic agent, anti-inflammatory agent, anti-febrile, anti-fungus agent, anti-influenza virus, influenza vaccine, steroid agent, anti-cancer substance, or anti-hypertensive agent.

The gain size of the mist supplied from the gas mist generating means into the mask member is preferably not larger than 10 μm.

Further, the gas mist generating means is shaped in dome of convex having a curved face toward an upper part with an inside curve and is provided with a gas mist discharge portion at the dome shaped top for discharging the gas mist.

The mask member has a gas mist supply port for introducing the gas mist supplied from the gas mist generating means into the cover means, and the gas mist supply port has advantageously a check valve inside.

The gas mist generating means has a gas mist supply pipe for supplying the gas mist into the mask member, and this gas mist supply pipe has preferably a filter to remove liquid drops attached to the inside of the pipe. Further, the whole or one part of the gas mist supply pipe is suitably composed of a cornice shaped pipe, and this gas mist supply pipe is provided with a check valve.

Further, the gas mist generating means has a storage for storing the gas mist, and this storage is desirably placed inside with one or plural sheets of pored plates for refining the gas mist. In the storage, there may be provided a gas supply port for directly supplying the gas from the gas supply means.

Preferably, the gas mist generation means is in advance sterilized.

Advantageous Effects of Invention

According to the gas mist mask device of the present invention, the physiological actions of oxygen or carbon dioxide are used for protecting the eyes and face of the human living organism from drying and chilling, so that it is possible to display effects such as activating a blood flow, rapidly relieving inflammation or heightening immunity.

Being composed of the simple structure and further very compact, carrying is possible and the gas mist bath can be easily taken for the eyes and face.

BRIEF DESCRIPTION OF DRAWINGS

FIG. 6 Perspective and typical views showing examples of the plates to be placed within the gas mist generator of the invention;

FIG. 8 A typical view showing one example of the eye mask of FIG. 1;

DESCRIPTION OF EMBODIMENTS

In the following description, explanations will be made to the embodiments of this invention, referring to the attached drawings.

First Embodiment

Figure 1:
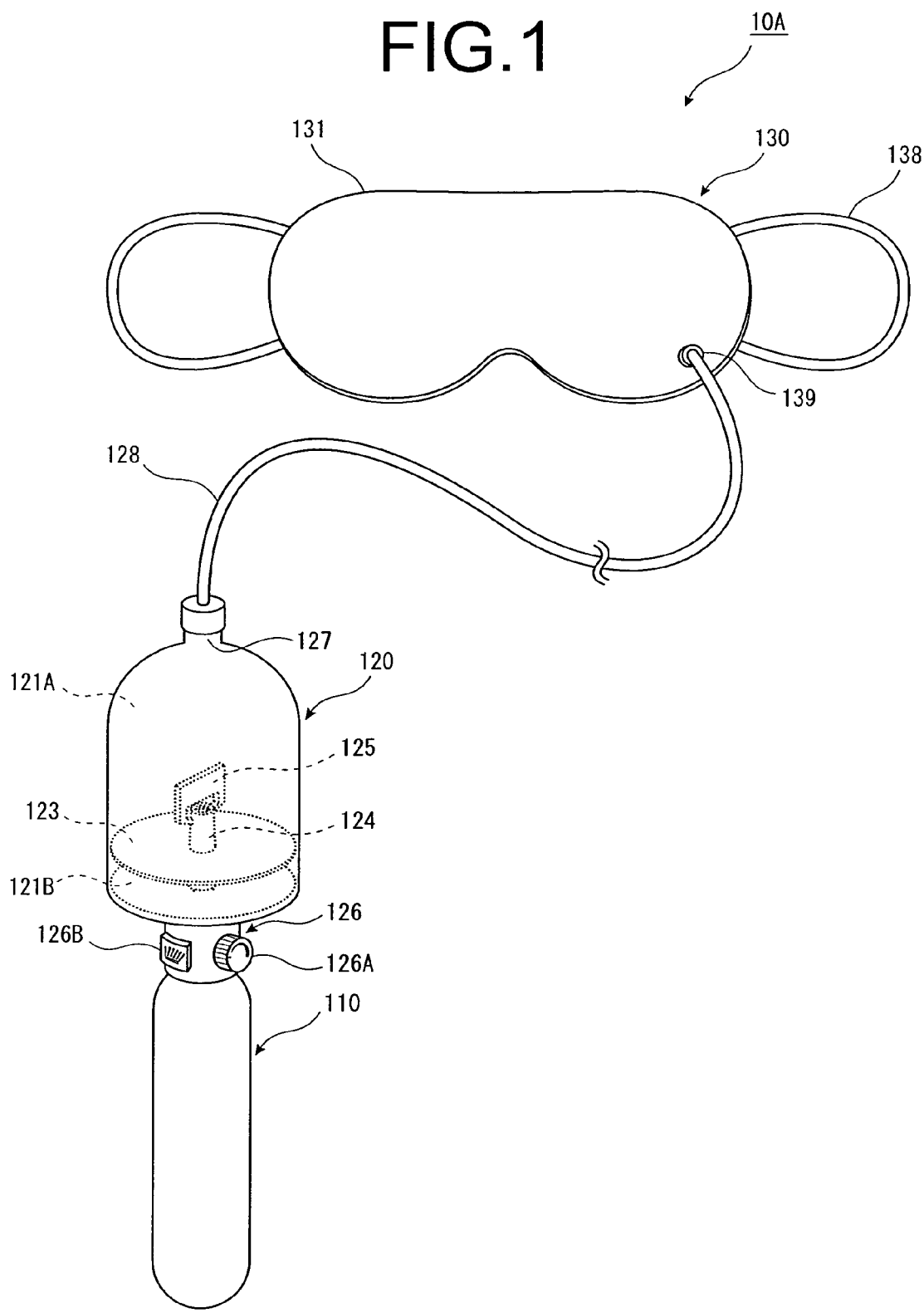
FIG. 1 A generally schematic view of the gas mist mask device depending on a first embodiment of the invention.

FIG. 1 is the generally schematic view of the gas mist mask device depending on the first embodiment of the invention. As shown herein, the gas mist mask device 10A of the present embodiment has the gas bomb 110 serving as the gas supply means, the gas mist generator 120 serving as the gas mist generation means and the eye mask 130 as the mask member.

With respect to the gas bomb 110 of supplying oxygen, carbon dioxide, or the mixed gas (called briefly as "gas" hereafter) of oxygen and carbon dioxide, the present embodiment employs a cartridge system in a small size, giving attention to portability. This small sized gas bomb 110 is, as shown in FIG. 1, attached to the gas bomb connection portion 126 of the gas mist generator 120 and supplies the gas into the gas mist generator 120 at predetermined pressure.

Figure 2:
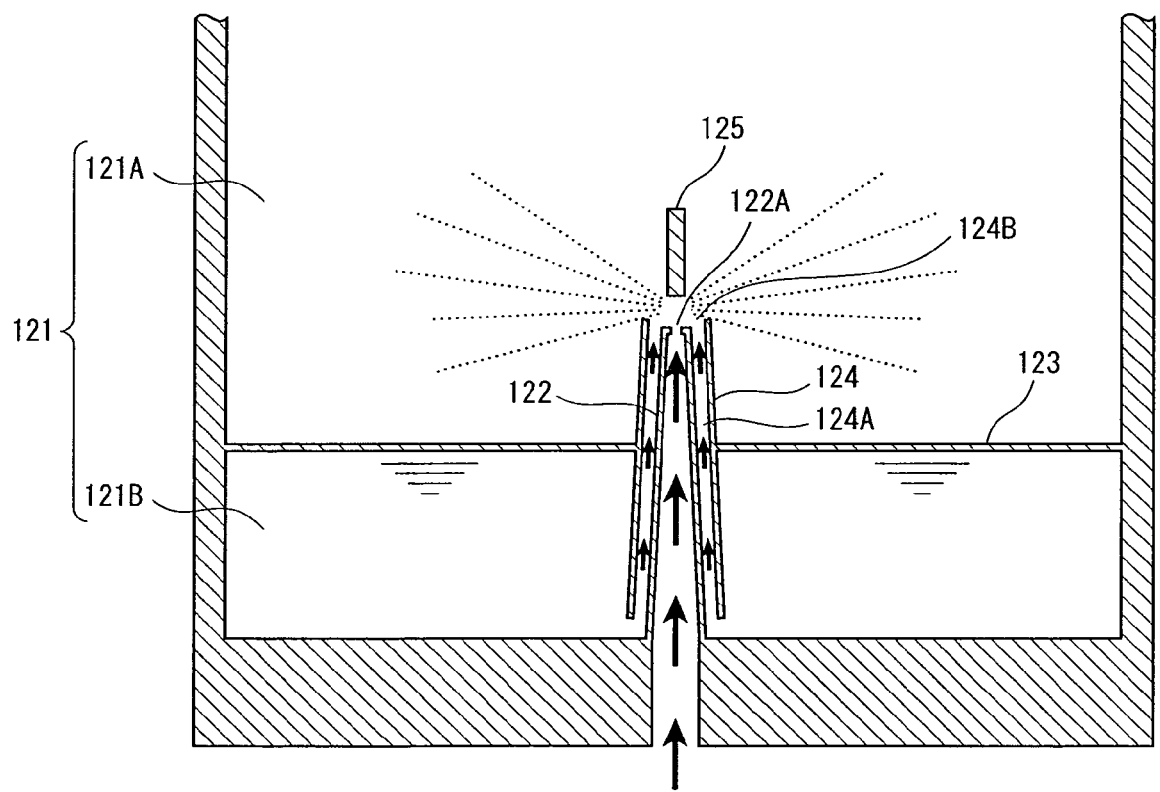
FIG. 2 A partially cross sectional and typical view of the gas mist generator of FIG. 1.
Figure 3:
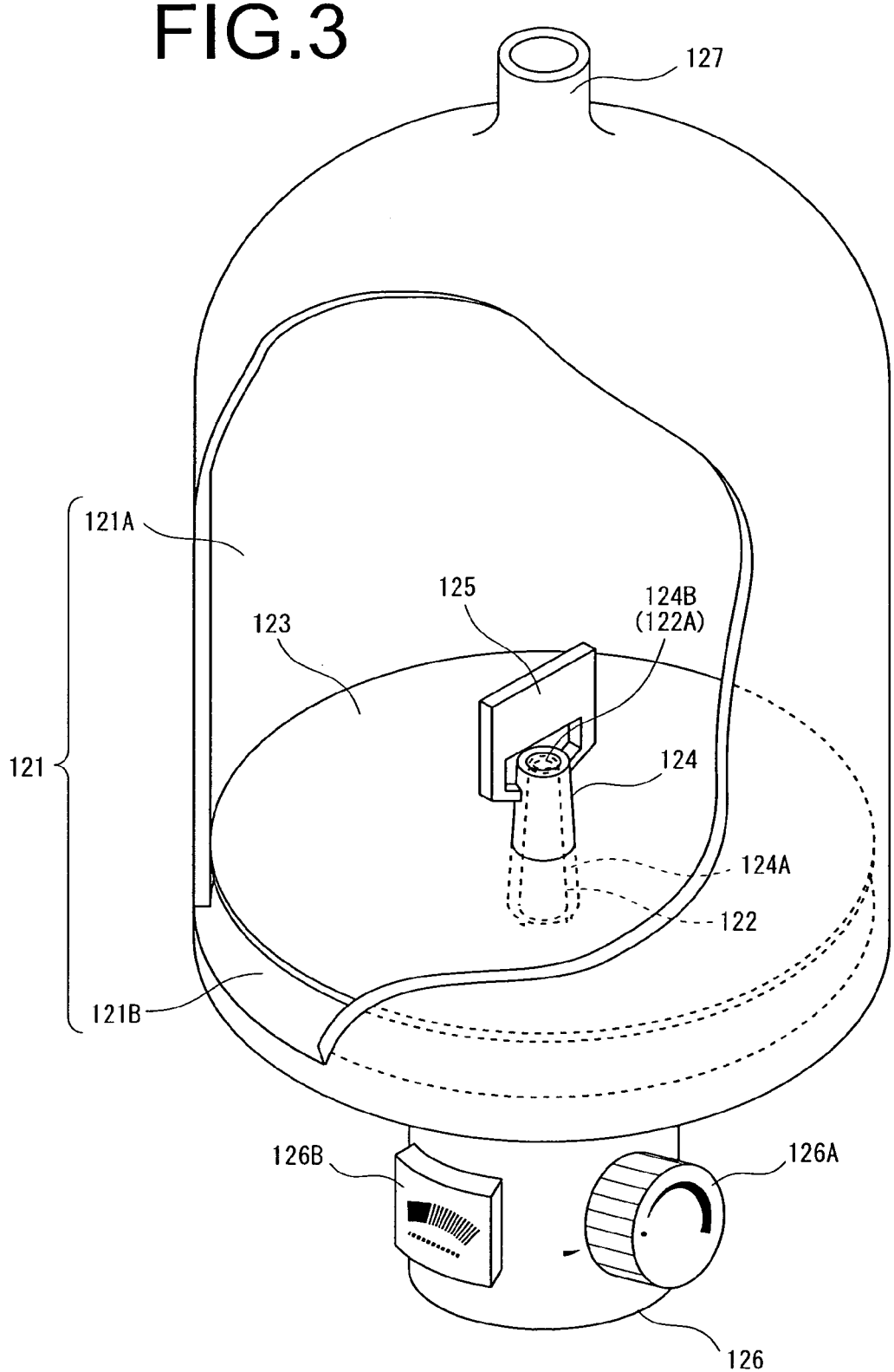
FIG. 3 A perspective view, partially in section, of the gas mist generator of FIG. 1.

The gas mist generator 120 stores inside a liquid, generates the gas mist by pulverizing and dissolving the liquid and the gas by means of high speed of the gas supplied from the gas bomb 110, and supplies this gas mist to the mask member (eye mask 130). FIGS. 2 and 3 illustrate the structure of the gas mist generator 120. As seeing therein, the gas mist generator 120 has the storage 121 composed of the gas mist storage 121A storing the gas mist and a liquid storage 121B storing the liquid, a nozzle 122 discharging the gas supplied from the gas bomb 110 out of a front end opening 122A, a liquid suction pipe forming member 124 defining a liquid suction pipe 124A sucking up the liquid stored in the liquid storage 121B up to the front end of the nozzle 122, a baffle 125 positioned in opposition to the front end opening 122A, a gas bomb connecting portion 126 connected to the gas bomb 110, and a gas mist discharge port 127 discharging the generated gas mist.

The storage 121 is, as shown in FIG. 3, sectioned into a gas mist storage 121A and a liquid storage 121B by a shielding sheet 123. The upper side (the side of the nozzle front end opening 122A) of the shielding plate 123 is the gas mist storage 121A storing the generated gas mist, while the lower side (the side of the gas bomb connecting portion 126) is the liquid storage 121B storing the liquid.

By the way, the shielding plate 123 serves to force up the liquid in the liquid suction pipe 124A by maintaining pressure in the liquid storage 121B highly than pressure in the gas mist storage 121A. Therefore, the shielding plate 123 may be positioned stationarily at a predetermined position of an inner wall of the liquid storage 121B, otherwise may be vertically movable in response to the level of a liquid surface in the liquid storage 121B. Further, depending on magnification of gas pressure issued from the front end opening 122A, the shielding plate 123 may not be furnished.

At the bottom center of the storage 121, a nozzle 122 is placed. The nozzle 122 communicates the bottom of the storage 121 and the gas bomb connecting portion 126, and is shaped to be almost circular cone toward an upper side from the bottom of the storage 121. The nozzle 122 is connected at its base end to the gas bomb connecting portion 126, to which the gas bomb 110 can be directly connected. The nozzle 122 projects at its front end to the side of the gas mist storage 121A, and can discharge the gas from the front end opening 122A.

The liquid suction pipe 124A is defined between the outer circumference of the nozzle 122 and the inner circumference of the liquid suction pipe forming member 124 of the almost circular cone being larger by a turn than the nozzle 122. That is, as shown in FIG. 2, by positioning as covering the liquid suction pipe forming member 124 of the nozzle 122, the liquid suction pipe 124A is defined between the outer circumference of the nozzle 122 and the inner circumference of the liquid suction pipe forming member 124. At this time, since a nail shaped projection (not showing) is provided at a base end of the liquid suction pipe forming member 124, a space is formed at a base of the liquid suction pipe forming member 124 and the bottom of the liquid storage 121B, so that the liquid stored in the liquid storage 121B is drawn up from this space by the liquid suction pipe 124A. In addition, the front end 124B of the liquid suction pipe forming member 124 opens nearly the front end opening 122A of the nozzle 122, and the liquid drawn up by the liquid suction pipe 124A collides against the gas flow discharged from the nozzle 122.

The baffle 125 is a member disposed at a position in opposition to the front end opening 122A of the nozzle 122 and the front end 124B of the liquid suction pipe forming member 124, and in the present embodiment, this is connected to the liquid suction pipe forming member 124. Otherwise, in order to secure the baffle 125, such a structure may be available which is connected to the shielding plate 123 and the inside of the storage 121, that is, the inside of the gas mist generator 120. The liquid suction pipe forming member 124 is connected to the shielding plate 123 at the nearly central part in the vertical directions. The shielding plate 123 is also connected at its outer circumference to the inside of the storage 121. Thus, desirably, the gas mist generator 120 is formed integrally as a whole.

The gas bomb connecting portion 126 communicates the base end of the nozzle 122 and has inside a regulator. The gas bomb connecting portion 126 is preferably so structured that the gas bomb 110 can be connected by one touch. This embodiment shows an example of furnishing the gas bomb connecting portion 126 with a dial switch 126A and a residual gauge 126B. The dial switch 126A can adjust on-off of the gas supply and flow rate by rotation. The residual gauge 126B shows the gas remaining amount of the gas bomb 110.

The gas mist generated in the gas mist generator 120 is fed into the eye mask main frame 131 from the connecting portion 139 through the gas mist supply pipe 128 connected to the gas mist discharge port 127. The gas mist supply pipe 128 is provided inside with a check valve for preventing a back flow of the gas mist, though not showing. In addition, the gas mist supply pipe 128 may be provided with a filter for removing extra liquid drops attached to the inside of the pipe, though not showing, either.

Figure 4:
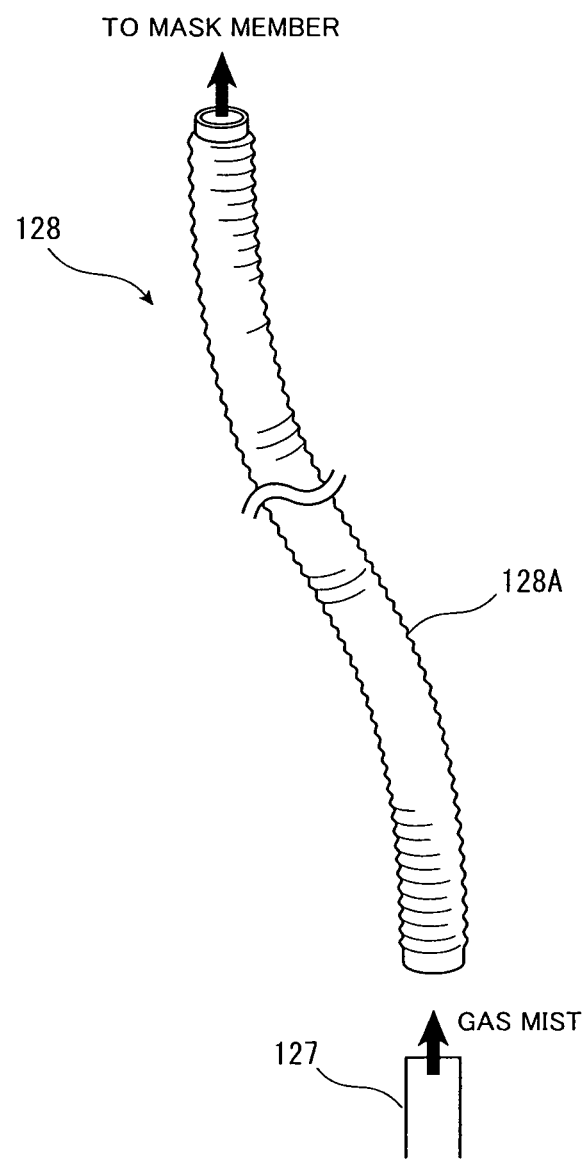
FIG. 4 A schematic view showing one example of the gas mist supply pipe used in the gas mist mask device of FIG. 1.

Further, if the gas mist supply pipe 128 is overall or partially composed of a soft cornice shaped pipe 128A of a large diameter as shown in FIG. 4, it may be freely bent and may be expanded so that a user of this system is not restricted in his action. Even if the gas mist flowing in the gas mist supply pipe 128 becomes gradually liquefied, the liquid can be removed through the concave and convex of the cornice.

The gas mist generator 120 is preferably in advance processed with a sterilizing treatment, and for using the present gas mist mask device 10, the liquid is desirably already stored in the gas mist generator 120. For example, in the liquid storage 121B, a predetermined liquid is in advance stored at a manufacturing stage (in a case of a disposal type). Preparing as disposal, the gas mist can be absorbed hygienically and simply. Otherwise, the storage 121 may be provided with a liquid pouring port or a liquid supplementing port for previously pouring the liquid there, or supplementing each time using it. It is convenient that a liquid supplementing port (not shown) having a cap is provided at an upper part of the gas mist storage 121A of the gas mist generator 120, and a liquid supplementing pipe or tube is provided between the liquid supplementing port and the liquid storage 121B.

Figure 5:
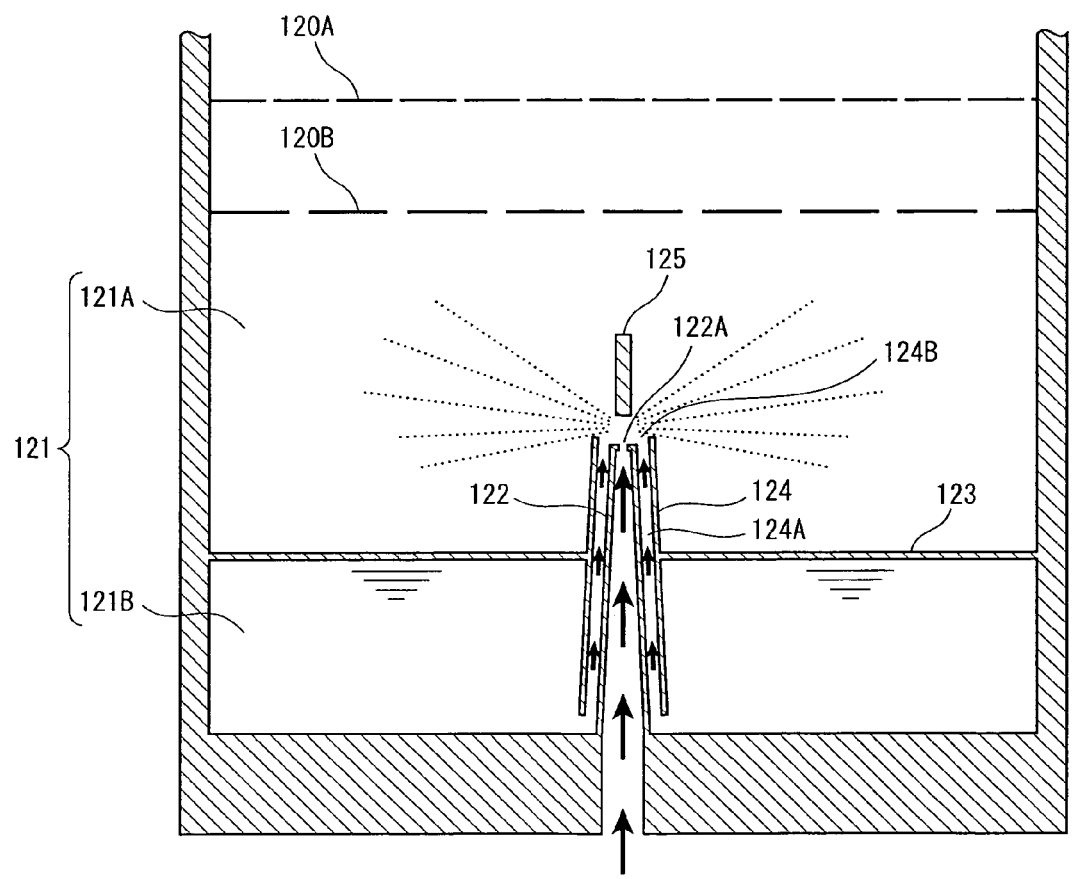
FIG. 5 A partially cross sectional and typical view showing another example of the gas mist generator of the invention.

In addition, as shown in FIG. 5, at the position above the nozzle 122 of the gas mist storage 121A, one or plural sheets (in FIG. 5, two sheets as an example) of plates 120A, 120B may be furnished. FIG. 6 shows the examples of the plates 120A, 120B. Thus, the plates 120A, 120B are formed with plural pores, and the generated gas mist is refined when passing through the pores. With respect to the upper plate 120A and the lower plate 120B, it is preferable that the diameters of the pores of the upper plate 120A are smaller than those of the pores of the lower plate 120B.

Herein, for the liquid stored in the liquid storage 121B, it is preferable to employ water, ionic water, physiological salt solution, ozone water, purified water or sterilized and purified water. In addition, these liquids may contain medicines effective to users' diseases or symptoms. For the medicines, there are enumerated, for example, anti-allergic agent, anti-inflammatory agent, anti-febrile and analgesic, anti-fungus agent, anti-influenza viral agent, influenza vaccines, steroid substance, anti-cancer drug, anti-hyper tensile agent. Further, these liquids are mixed with single or plurality of menthol having a cooling action; vitamin E accelerating circulation of the blood; vitamin C derivative easily absorbed to a skin tissue and having a high skin beautifying effect; retinol normalizing a skin heratinizing action and protecting the mucous membrane; anaesthetic moderating irritation to the mucous membrane; cyclodextrin removing odor; photocatalysis having sterilizing and anti-phlogistic effect or a complex of photocatalysis and apatite; hyaluronic acid having excellent water holding capacity and a skin moisture retention effect; coenzyme Q10 activating cells and heightening immunization; a seed oil containing anti-oxidation substance, or much nutrient; propolith having anti-oxidation function, anti-fungus function, anti-inflammatory function, pain-killing function, anesthetic function, and immunity function. Thus, those substances are possible to generate synergistic effects by coupling with a gas physiological action. Otherwise, it is possible to add silica or povidone-iodine.

Figure 7:
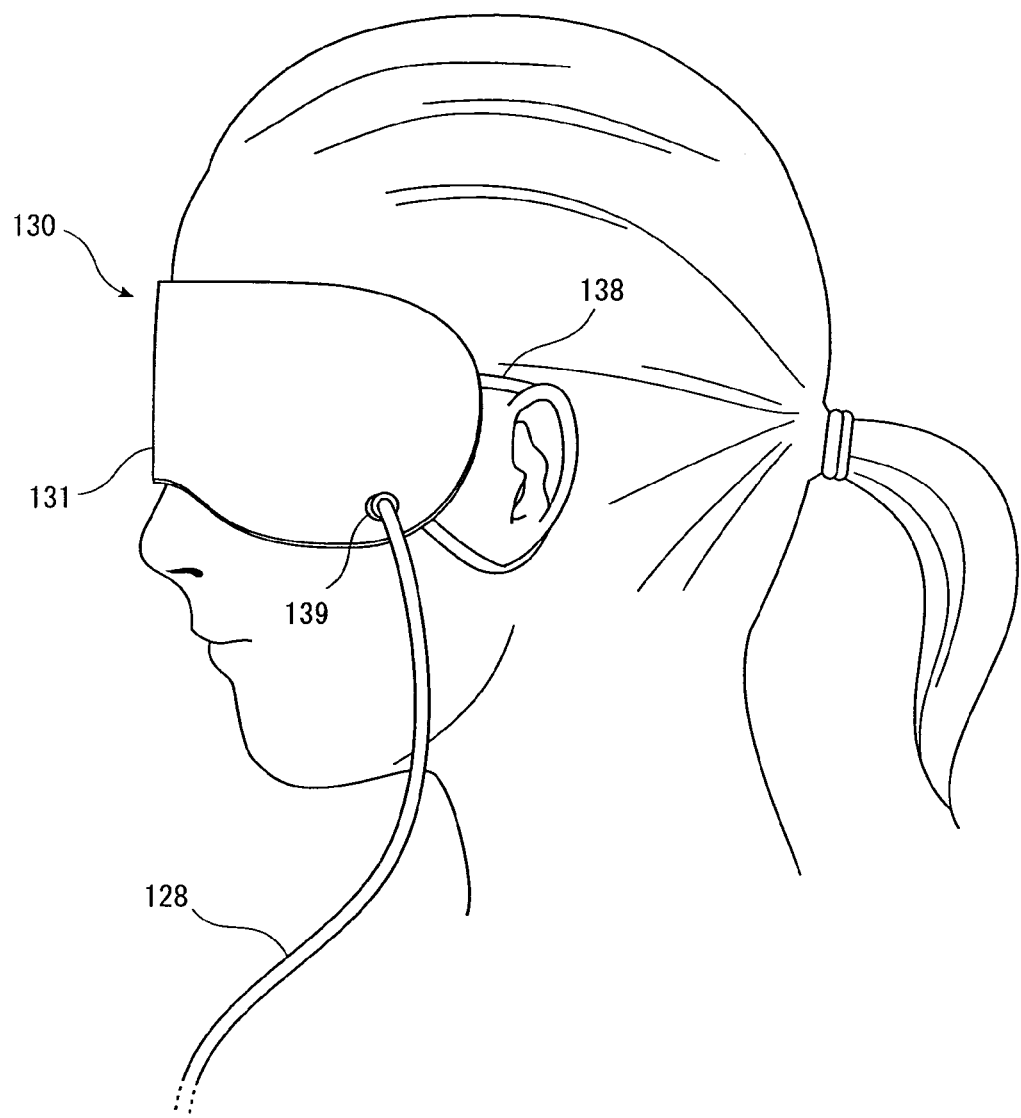
FIG. 7 A typical view showing an example of a condition attaching the eye mask of FIG. 1.

The eye mask 130 is, as shown in FIG. 1, composed of an eye mask main frame 131 having a shape of covering a user's both eyes and those surrounds as well as holding parts 138 for securing the eye mask main frame 131 to the user's eyes. FIG. 7 shows a condition of attaching this eye mask 130. As shown herein, by catching the holding parts 138 on the user's ears, the eye mask main frame 131 can be secured to the user's both eyes and those surrounds.

The eye mask main frame 131 has a connecting portion (gas mist supply port) 139 for supplying the gas mist generated in the gas mist generator 120 into the eye mask main frame 131. To this connecting portion 139, a gas mist supply pipe 128 is connected. Although not showing, the inside of the connecting portion 139 is formed with a check valve for preventing back flow of the gas mist.

The eye mask main frame 131 has, as seen in FIG. 8(a), a structure of putting an inside sheet (first sheet) 132 on an outside sheet (second sheet) 133. The inside sheet 132 is composed of a material having high air-permeability and moisture-permeability, while the outside sheet 133 is composed of a material having non air-permeability and non moisture-permeability, and when attaching, the inside sheet 132 is made opposite to the skin. By the way, the inside sheet 132 and the outside sheet 133 are, as seen in FIG. 8(b), joined by a connected portion 135 all over a rim, and between both sheets 132 and 133 joined at the fringe by the connected portion 135, a space 134 is defined. In this space 134, a heating member 136 is inserted. The above mentioned connecting portion 139 communicates this space 134 into which the gas mist generated in the gas mist generator 120 is supplied. The supplied gas mist passes through the inside sheet 132 of high air-permeability and moisture-permeability, and contacts the user's eyes, or skin and mucous membrane around the eyes.

For the heating member 136, as used in an existing disposable pocket heater, it is suitable to employ such a material having an oxidation heating substance as iron powders in an air-permeable bag, provided that, since such a heating member 136 is used only once because of being disposable and in case the heating member 136 has the structure of being in advance sealed in the space 134 as shown in FIG. 8, the whole of the eye mask 130 must be made disposable. Further, for preventing oxidation heating of the heating member 136 while non-using, the eye mask 130 must be packed in an outer wrapping (not shown) of non air-permeability under an anoxia (or low oxygen) condition. Incidentally, for eliminating wastefulness of throwing away, a sheet shaped heater can be used as the heating member 136 to be the eye mask 130 being not disposable.

Figure 9:
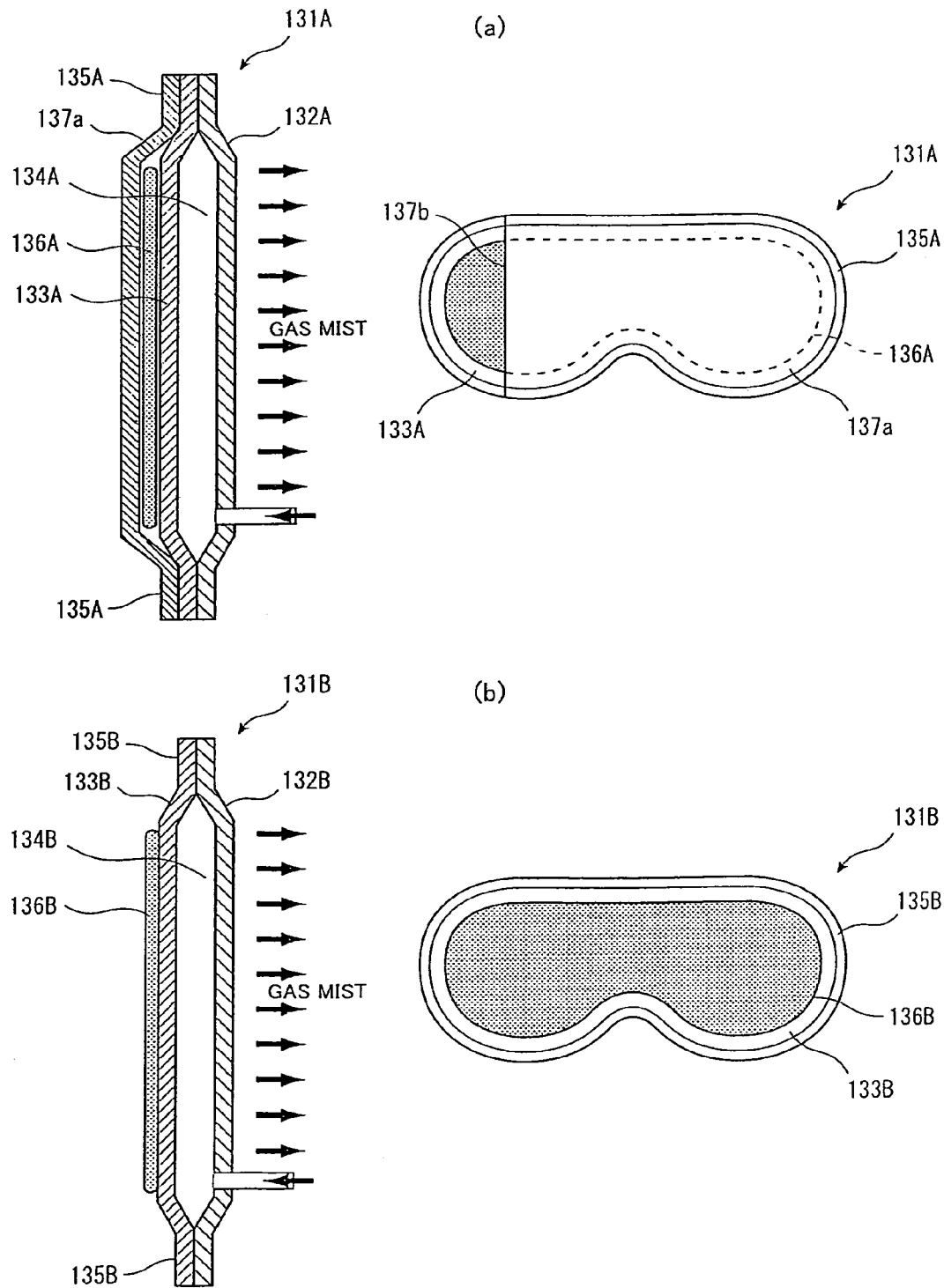
FIG. 9 Typical views showing the other examples of the eye mask of FIG. 1.

Otherwise, the eye mask main frame 131 may be also sufficient as shown in FIG. 9. The eye mask main frame 131A shown in FIG. 9(a) has a structure that the inside sheet 132A, the outside sheet 133A and a further air-permeable 137a are piled and joined together at the connected portion 135, provided that the air-permeable 137a is not joined all over the rim but opened at one part which will be an in-and-out port 137b of the heating member 136A. When using the gas mist main frame 131A, the heating member 136A is inserted into the in-and-out port 137b between the air-permeable sheet 137a and the outside sheet 133A.

In the eye mask main frame 131B shown in FIG. 9(b), the heating member 136B is not inserted into the space 134B between the inside sheet 132B and the outside sheet 133B, but the heating member 136B is pasted with adhering material (for example, a both face adhesive tape) on the outside of the outside sheet 133B. After using, the heating member 136B is stripped to disuse.

As seeing FIG. 9, in a case of a structure detachably attaching the heating members 136A, 136B to the eye mask main frames 131A, 131B, only the heating members 136A, 136B composed of the material having the oxidation heating substance as iron powders are packed in the outer wrapping (not shown) of non air-permeability under the anoxia (or low oxygen) condition, and at each time of using, they are attached to the eye mask main frames 131A, 131B, and after using, the heating members 136A, 136B are removed from the eye mask main frames 131A, 131B and thrown away. In short, since only the heating members 136A, 136B are made disposable and the eye mask main frames 131A, 131B can be re-used, they are very economical. In addition, the heating members 136A, 136B may be sheet-shaped heaters.

Next, for taking the gas mist bath with the gas mist mask device 10A of the above mentioned first embodiment, at first, the eye mask 130 is fixed to the user's eyes, and the heating member 136 is worked (the heating member 136 is taken out from an outer wrapping to effect oxidation heating, and the heater is turned on). As shown in FIG. 9, in the case of eye mask main frames 131A, 131B, the heating member 136 is set on the eye mask main frame 131. Subsequently, under a condition of already storing the liquid in the liquid storage 121B, the gas bomb 110 is set to the gas bomb connecting portion 126 of the gas mist generator 120. When turning a dial switch 126A of the gas bomb connecting portion 126, the gas starts to go into the nozzle 122. Further, the gas flowing rate is adjusted by the dial switch 126A. Since the nozzle 122 reduces the diameter toward the front end as shown in FIG. 2, the gas from the gas bomb 110 increases the flowing speed and is discharged. The liquid is sucked up within the liquid suction pipe 124A by negative pressure caused by air flow at this time, and collides against the baffle at its lower end. Desirably, the diameter of the mist generated by this collision is fine, and concretely, best is smaller than 10 μm. The thus finely pulverized mist can display effects of minus ion.

The generated gas mist spreads within the gas mist storage 121A and is discharged from the gas mist discharge port 127 following a convection of the gas. The gas mist storage 121A is desirably shaped in dome of convex having a curved face toward its upper portion as shown in FIG. 1. At the top portion of the dome shape, the gas mist discharge port 127 is formed. By making such a shape, it is possible to store more the gas mist, while avoiding that the mist contacts the upper portion of the interior wall of the gas mist storage 121A, goes back to the liquid and drops.

The gas mist discharged from the gas mist discharge port 127 passes through the gas mist supply pipe 128 and goes into eye mask main frame 131 via the connecting portion 139. Thereby, the gas mist bathing is carried out.

Second Embodiment

The above first embodiment has shown, as the mask member, the example of using the eye mask 130 covering the eyes and those surroundings, and the present embodiment will explain an example of using a face mask covering the whole of the face.

Figure 10:
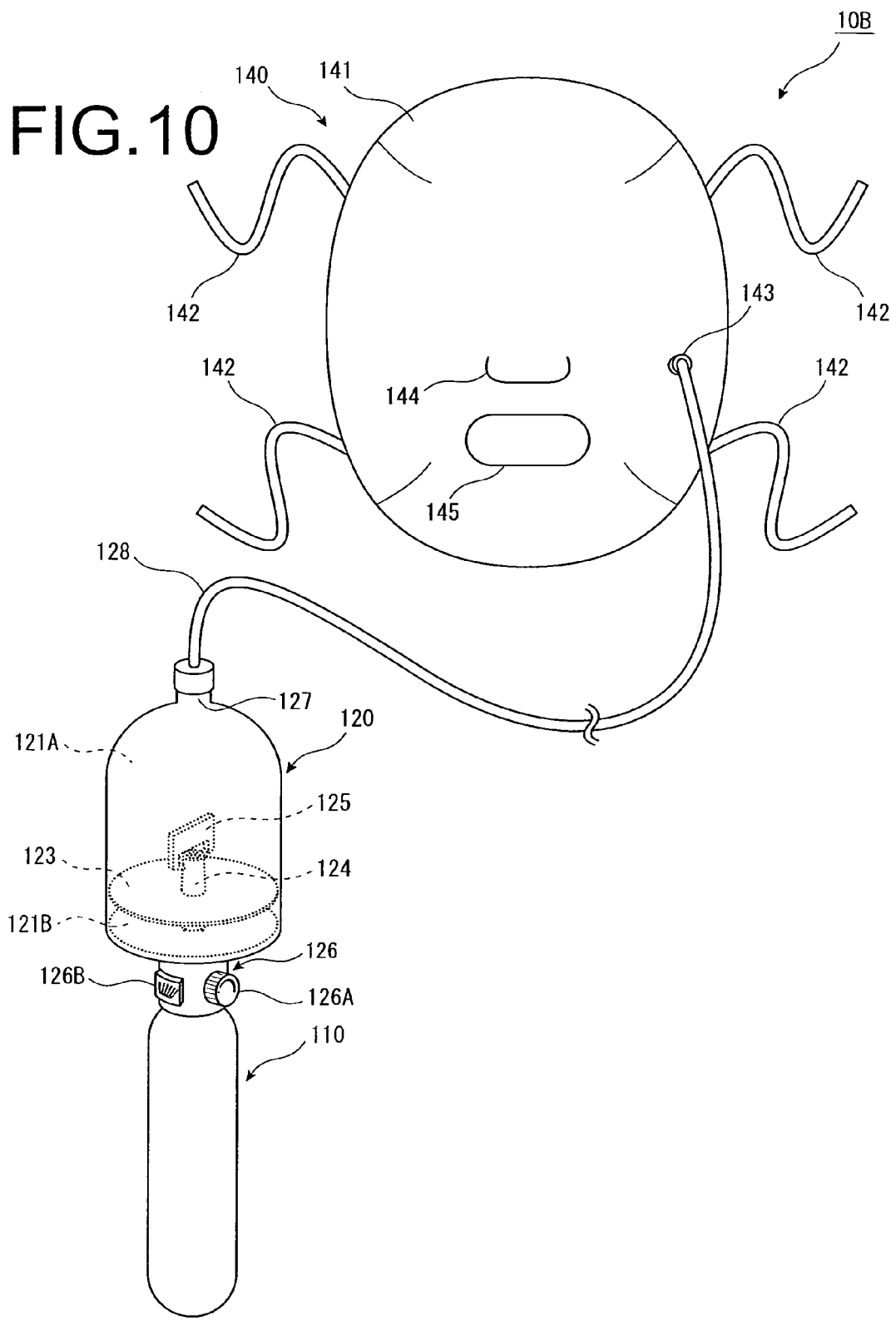
FIG. 10 A generally schematic view of the gas mist mask device depending on a second embodiment of the invention.

FIG. 10 is the generally schematic view of the gas mist mask device depending on the second embodiment of this invention. As to the same parts as those of the first embodiment shown in FIG. 1, the same numerals will be given, and detailed explanation will be omitted.

As shown in FIG. 10, the gas mist mask device 10B of the present embodiment has a gas bomb (gas supply means) 110, the gas mist generator (gas mist generating means) 120, and the face mask (mask member) 140.

Figure 11:
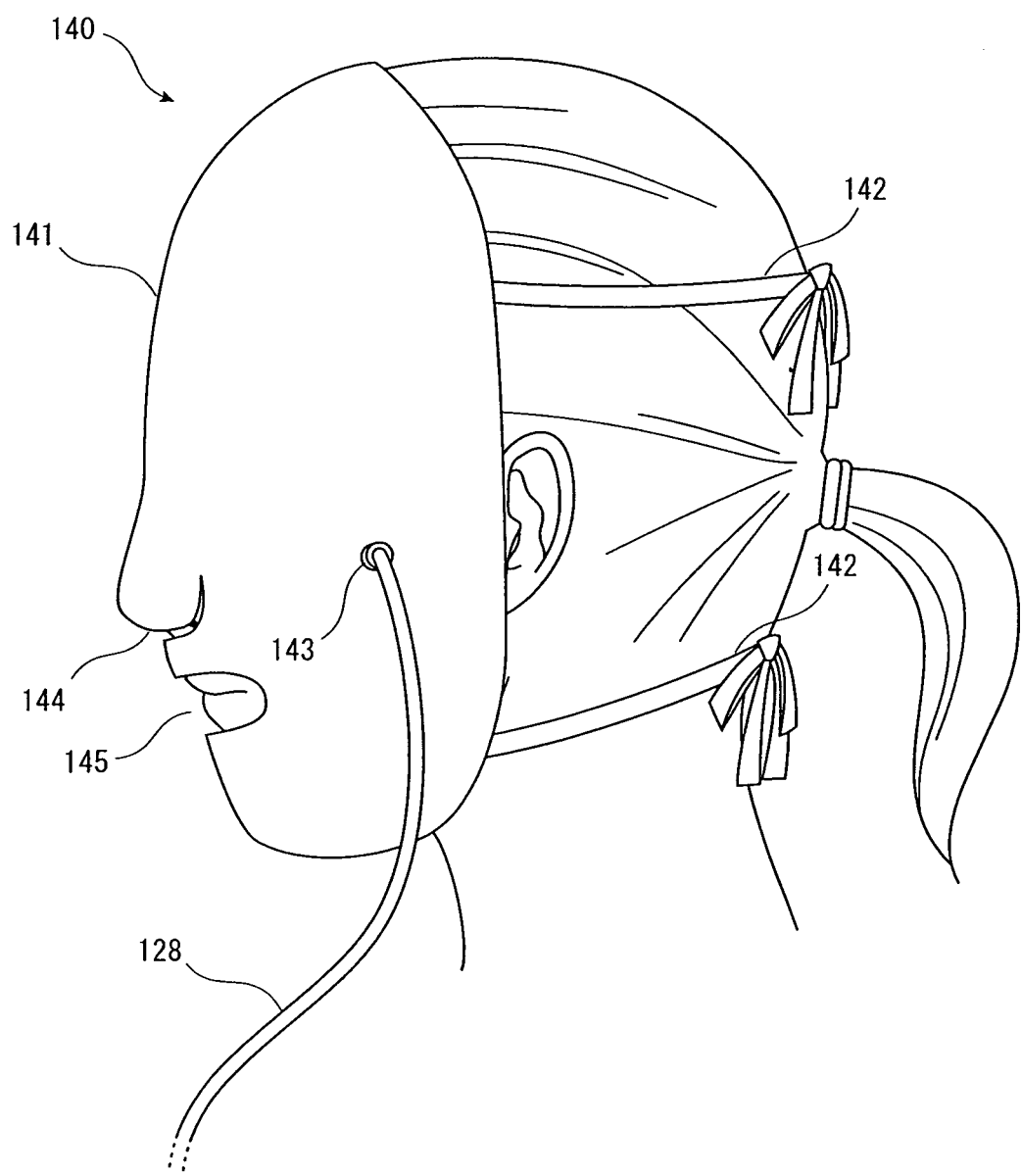
FIG. 11 A typical view showing an example of a condition attaching the face mask of FIG. 10.

The face mask 140 is composed of a face mask main frame 141 having a shape covering the user's face and holding parts (herein, as an example, strings) 142. FIG. 11 shows a condition of putting the face mask 140. As shown, by knotting the strings 142 at the user's occipital region, the face mask main frame 141 can be secured as covering the user's face.

The face mask main frame 141 has a connecting portion (gas mist supply port) 143 for supplying the gas mist generated in the gas mist generator 120 into the face mask main frame 141. To this connecting portion 143, a gas mist supply pipe 128 is connected. The inside of the connecting portion 143 is formed with a check valve for preventing back flow of the gas mist.

Since the face mask main frame 141 covers the whole of the user's face, an opening for breathing is formed. Herein, shown is an example forming an opening for nose 144 and an opening for mouth 145. For the face mask main frame 141, a stereoscopic shape is desirable so that it fits following curves of the user's face.

The face mask main frame 141 has also, similarly to the eye mask main frame 131 in the embodiment shown in FIG. 1, a structure of putting an inside sheet (first sheet) of high air-permeability and high moisture-permeability on an outside sheet (second sheet) of non air-permeability and non moisture-permeability (refer to FIG. 3). The periphery of the face mask main frame 141 and the edges of the openings 144, 145 are connected, and between both sheets surrounded at the connected edges, spaces are formed, into which the heating member is inserted (refer to FIG. 8(a)). The above mentioned connecting portion 143 communicates this space into which the gas mist generated in the gas mist generator 120 is supplied. The supplied gas mist passes through the inside sheet of high air-permeability and moisture-permeability, and contacts the user's eyes, skin and mucous membrane of other parts.

For the heating member 136, as used in an existing disposable pocket heater, it is suitable to employ such a material having the oxidation heating substance as iron powders in the air-permeable bag, and the sheet shaped heater may be available. In addition, the heating member may be held between the inside sheet and the outside sheet (refer to FIG. 8(a)), or positioned at the side of the outside sheet (refer to FIG. 9). The face mask 140 may be disposable or repeatedly used. In case of being disposable, the whole of the face mask 140 may be disposable, or only the heating member may be disposable, provided that since the face mask has a more complicated shape than that of the eye mask, and as shown in FIG. 9(a), in case the heating member is inserted between the outside sheet and the air-permeable sheet, it is suitable to divide the heating member into several parts and insert them into the plural in-and-out ports.

Third Embodiment

The above first and second embodiments have shown the example as the gas supply means using the small sized gas bomb 110 of the cartridge system, and the present embodiment will show an example using a gas supply device of a stationary type.

Figure 12:
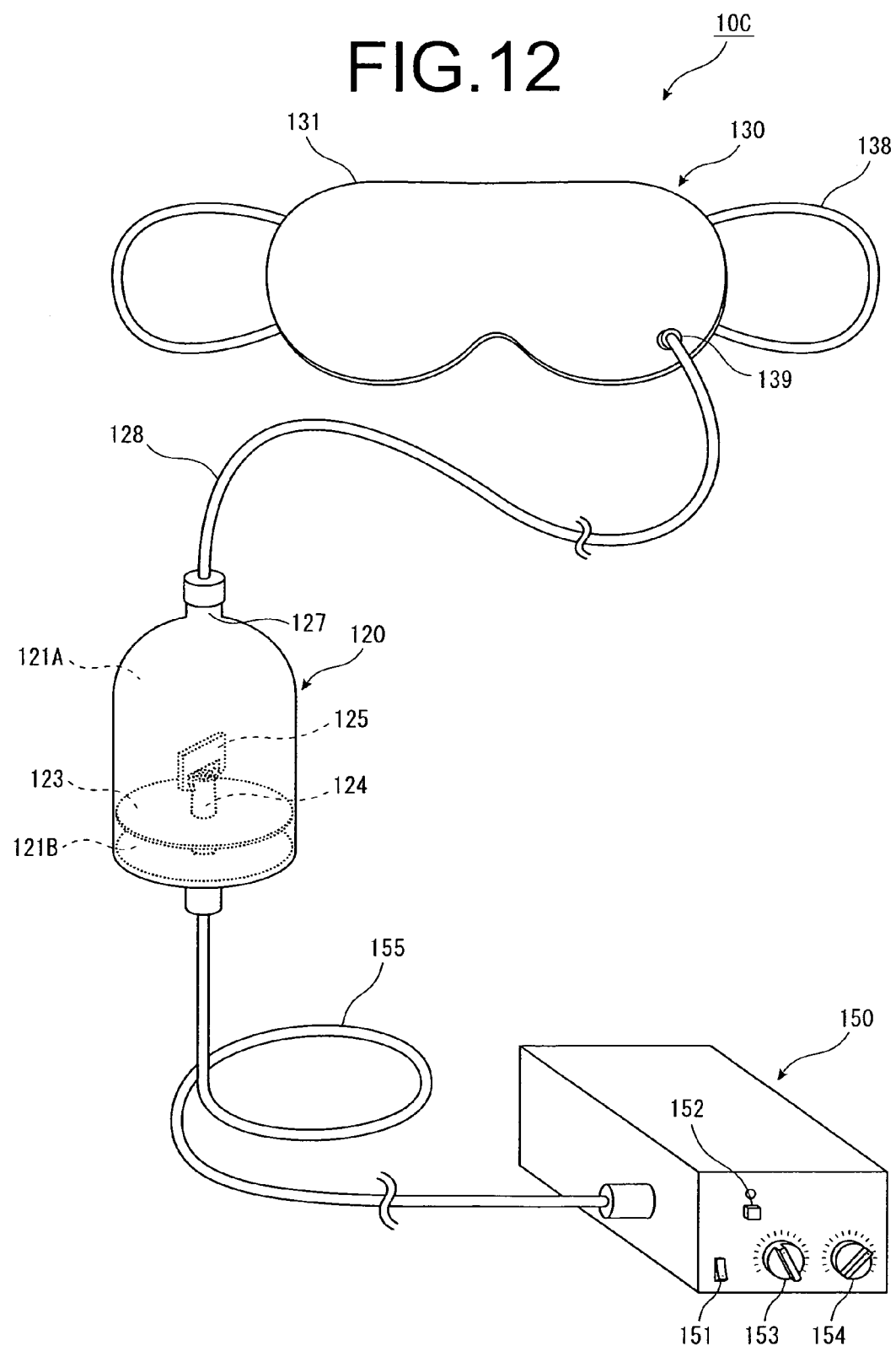
FIG. 12 A generally schematic view of the gas mist mask device depending on a third embodiment of the invention.

FIG. 12 is the generally schematic view of the gas mist mask depending on the third embodiment of this invention. As to the same parts as those of the first embodiment shown in FIG. 1, the same numerals will be given, and detailed explanation will be omitted.

As shown in FIG. 12, the gas mist mask device 10C has a gas supply device (gas supply means) 150, the gas mist generator (gas mist generating means) 120, and the eye mask (mask member) 130.

The gas supply device 150 is a stationary typed device of supplying the gas (oxygen, carbon dioxide or the mixed gas of oxygen and carbon dioxide) into the gas mist generator 120 at predetermined pressure. Its inside is built-in with the gas bomb (not shown), and may be built-in with a compressor, otherwise may be connected to an outside gas bomb.

The gas supply device 150 is, for example as shown in FIG. 12, provided with an electric power source 151, gas supply ON/OFF switch 152, OFF timer (gas supply time setting part) 153, and gas supply pressure adjusting part 154. The gas supply device 150 and the gas mist generator 120 are connected via the gas supply pipe 155. The OFF timer 153 is for setting the gas supplying time, and when a set time passes away, it automatically stops a gas supply. The gas supply pressure adjusting part 154 can arbitrarily set the gas supplying pressure. In this manner, since the gas supply means is possible to set the gas supplying time or pressure, its using scope can be broadened. Other than this, it is sufficient to furnish a switch for separately supplying carbon dioxide and oxygen, or furnish the gas mixing ratio setting part. It is thereby possible to arbitrarily set the mixing ratio of carbon dioxide and oxygen, so that the user's requires can be replied at will.

Figure 13:
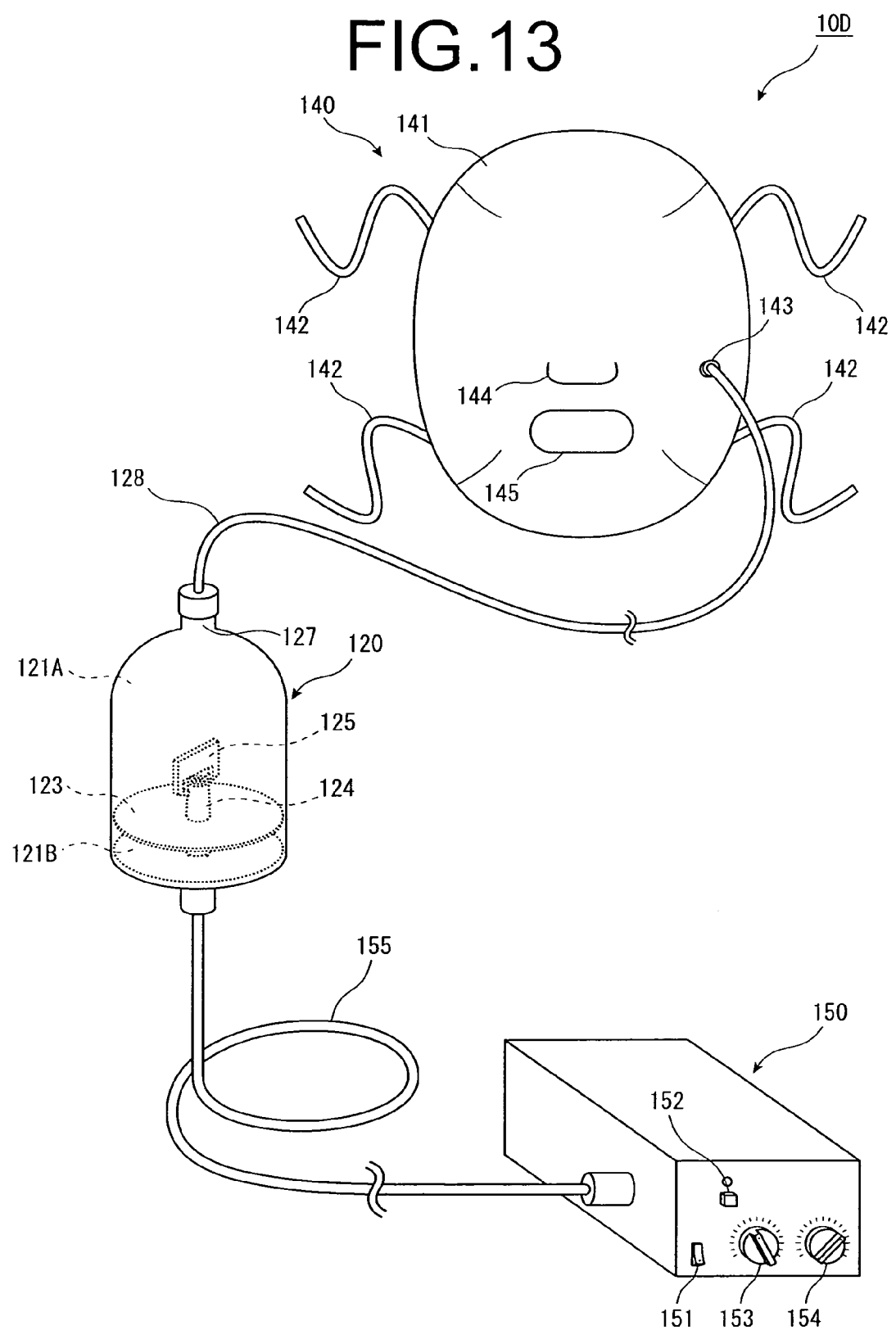
FIG. 13 A typical view showing the other example of the mask member of FIG. 10.

The above reference has shown the example of using the eye mask as the mask member covering the eyes and the surrounds, but the gas mist mask device 10D using the face mask 140 covering the whole of the face as shown in FIG. 13 is sufficient (as to the detail of the face mask 140, refer to the second embodiment).

Fourth Embodiment

The above third embodiment has shown the example where one gas mist generator 120 is connected with one mask member 130, 140 and the present embodiment will show a structure of connecting a plurality of mask members.

Figure 14:
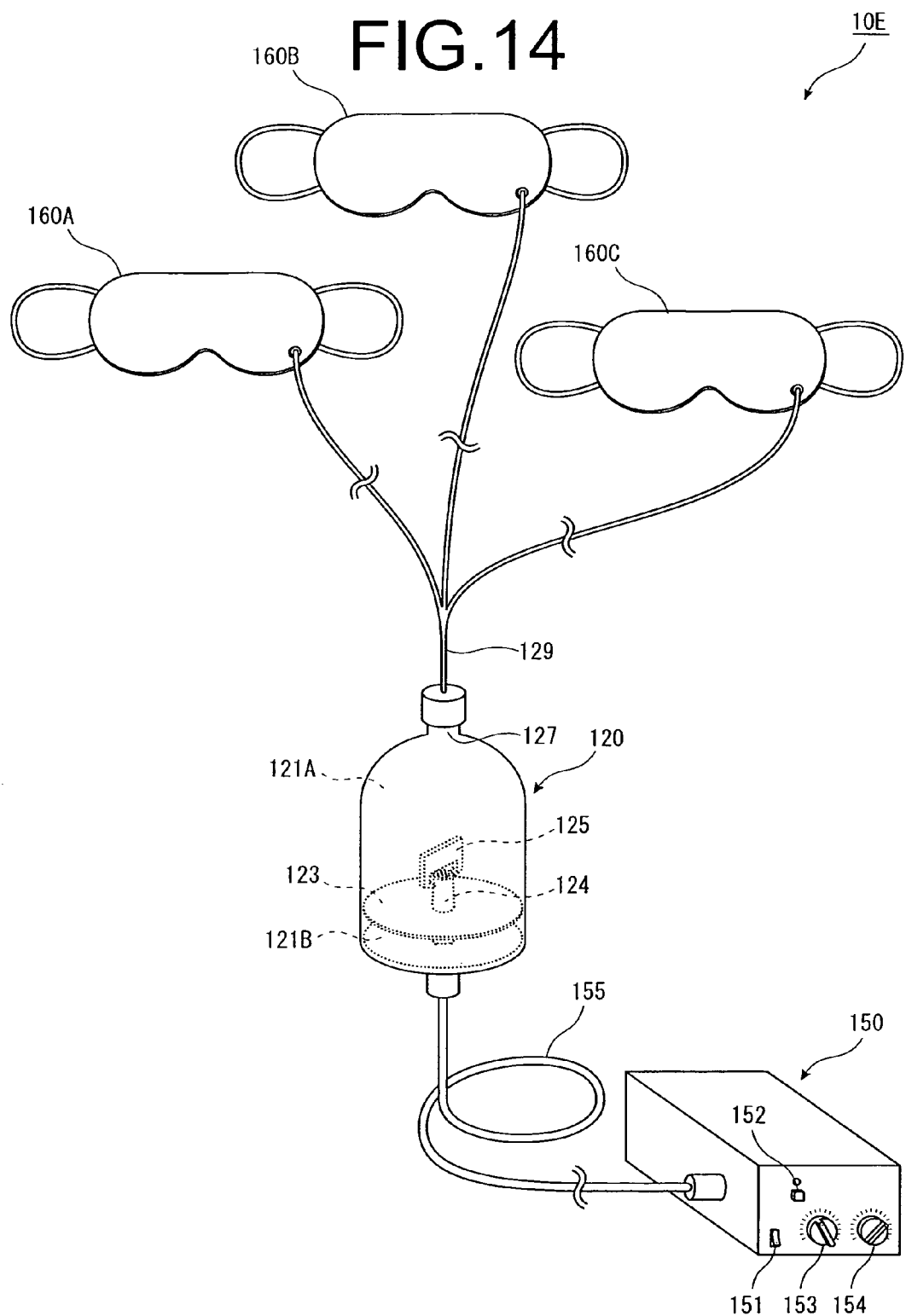
FIG. 14 A generally schematic view of the gas mist mask device depending on a fourth embodiment of the invention.

FIG. 14 is the generally schematic view of the gas mist mask device depending on the fourth embodiment of this invention. As to the same parts as those of the embodiment shown in FIGS. 1 to 13, the same numerals will be given, and detailed explanation will be omitted.

As shown in FIG. 14, the gas mist mask device 10E has the gas supply device (gas supply means) 150, the gas mist generator (gas mist generating means) 120, and plural mask members (eye masks) 160.

The present embodiment equips a gas mist supply pipe 129 diverging into a plurality (herein, three) of pipes between the gas mist generator 120 and a plurality (herein, three) of mask members (as examples, eye mask or a face mask will do) 160A, 160B, 160C. It is thereby possible to connect the plurality (herein, three) of mask members 160A, 160B, 160C to one gas supply device 150 and the gas mist generator 120. At this time, the gas supply device 150 adjusts gas supplying pressure by the gas supply pressure adjusting part 154 such that the gas mist bathing can be performed optimally in each of the plural mask members 160A, 160B, 160C.

Herein, the gas mist supply pipe 129 may be inside provided with the check valve for preventing the back flow of the gas mist, though not illustrated. Further, the gas mist supply pipe 129 may be furnished inside with the filter for removing surplus liquid drops, though not illustrated. The gas mist supply pipe 129 may be composed wholly or partially with the soft and cornice shaped pipe of large diameter.

The present embodiment has illustrated the example using the gas mist supply pipes 129 diverging into the plurality of pipes, and may provide a plurality of gas mist discharge ports in the gas mist generator, or provide diverged plural pipes on the way of the gas mist pipes for supplying the gas mist into the plural mask members.

Fifth Embodiment

The above embodiment has the structure of supplying the gas from the nozzle 122 only into the gas mist generator 120, but the present embodiment will refer to a structure having a gas supply inlet different from the nozzle in the gas mist generator.

Figure 15:
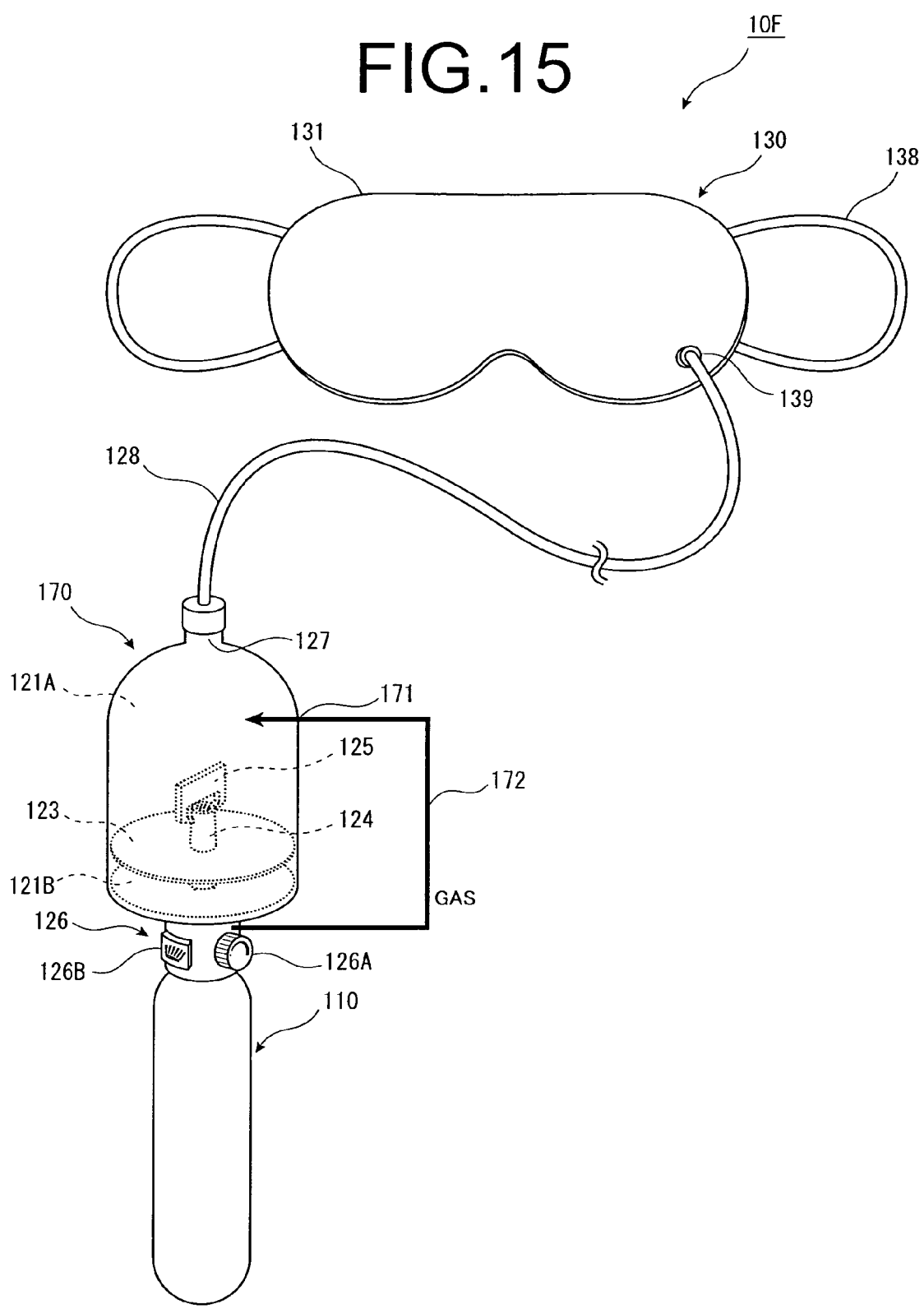
FIG. 15 A generally schematic view of the gas mist mask device depending on a fifth embodiment of the invention.

FIG. 15 is the whole schematic view of the gas mist mask device depending on the fifth embodiment of this invention. As to the same parts as those of the embodiment shown in FIGS. 1 to 14, the same numerals will be given, and detailed explanation will be omitted.

As shown in FIG. 15, the gas mist mask device 10F of this embodiment has the gas bomb (gas supply means) 110, the gas mist generator (gas mist generating means) 170, and the eye mask (eye mask) 130.

The gas mist generator 170 of this embodiment is provided with the gas supply port 171 and the gas supply port 172 supplying the gas from the gas bomb connecting portion 126 to the gas supply port 171.

The gas from the gas bomb 110 is supplied to the nozzle 126 within the gas mist generator 170 and, at the same time, also to the gas mist storage 121A from the gas supply port 171 via the gas supply pipe 172 from the gas bomb connecting portion 126. The gas supply port 171 or the gas supply pipe 172 are desirably furnished with a means (switch or the like) for starting or stopping gas supply from the gas bomb 110.

The above reference has explained the example of applying the small sized gas bomb 110 of the cartridge system as the gas supply means, and also can apply to the gas supply means 150 of the stationary type. In such a case, the gas supply pipe 172 may be directly connected to the gas supply means 150, or may be connected to the gas supply pipe 155 of the gas supply means 150.

Each of the above explained embodiments has illustrated the structure where the gas mist supply port (connecting portion) is only one for introducing the gas mist into the mask members 130, 140, 160, but there may be provided plural gas mist supply ports (connecting portions) for introducing the gas mist from plural places. A position for placing the gas mist supply port (connecting portion) is not limited to the shown place and can be determined arbitrarily.

In the above embodiments, as the parts of holding the mask members 130, 140, 160 to the eyes or the face, the ear holder or strings are enumerated, and others are various as belts, face-fasteners and so on.

According to the gas mist mask device of the present invention, the physiological actions of oxygen or carbon dioxide are used for protecting the eyes and face of the human living organism from drying and chilling, so that it is possible to display effects such as activating a blood flow, rapidly relieving inflammation or heightening immunity.

Being composed of a simple structure and further very compact, carrying is possible, and the gas mist bath can be easily taken to the eyes and face.

The above reference has explained the embodiments of the invention, but is not limited to the above embodiments, and so far as not deviating from the subject matter of the invention, various kinds of embodiments are, of course, available.

INDUSTRIAL APPLICABILITY

The present invention relates to the gas mist mask device for causing the gas mist to contact the face and eyes of the human living organism, which is prepared by pulverizing and solving oxygen, carbon dioxide, otherwise the mixed gas of oxygen and carbon dioxide, and liquid, bringing about the industrial availability.

REFERENCE SIGNS LIST 10A, 10B, 10C, 10D, 10E, 10F: gas mist mask device
110: gas bomb
120: gas mist generator
120A, 120B: plate
121: storage
121A: gas mist storage
121B: liquid storage
122: nozzle
122A: front end opening
123: shielding sheet
124A: liquid suction pipe
124: liquid suction pipe forming member
125: baffle
126: gas bomb connecting portion
126A: dial switch
126B: residual amount gauge
127: gas mist discharge port
128: gas mist supply pipe
128A: cornice shaped pipe
129: gas mist supply pipe
130: eye mask
131, 131A, 131B: eye mask main frame
132, 132A, 132B: inside sheet
133, 133A, 133B: outside sheet
134, 134A, 134B: space
135, 135A, 135B: connected portion
136, 136A, 136B: heating member
137a: air passing sheet
137b: in-and-out-port
138: holding parts
139: connecting portion
140: face mask
141: face mask main frame
142: holding parts
143: connecting portion
144, 145: opening
150: gas supply device
151: source switch
152: gas supply ON/OFF switch
153: OFF self-timer
154: gas supplying pressure adjustor
155: gas supply pipe
160: plural mask members
160A, 160B, 160C: mask member
170: gas mist generator
171: gas supply port
172: gas supply pipe

The invention claimed is:

1. A gas mist mask device, comprising:
a gas supply device for supplying a gas including oxygen, carbon dioxide, or a mixed gas of oxygen and carbon dioxide,
a gas mist generating device connected to the gas supply device for storing a liquid inside thereof and generating a gas mist prepared by pulverizing and dissolving the liquid and the gas, the gas mist generating device having a gas mist storage, a liquid storage adjacent to the gas mist storage, a shielding sheet separating the gas mist storage and the liquid storage, a nozzle connected to the gas supply device and projecting into the gas mist storage to discharge the gas in the gas mist storage, and a liquid suction pipe surrounding the nozzle to take up the liquid to the gas mist storage, and
a mask member having a mask main frame including a first sheet permeable to the gas mist and a second sheet impermeable to the gas mist and facing one side of the first sheet to create a space where the gas mist is supplied from the gas mist generating device, and a holding part for securing the mask main frame such that another side of the first sheet is configured to face eyes or a face of a human living organism, the gas mist from the gas mist generating device being configured to supply to the eyes or the face through the first sheet,
wherein the gas mist generating device is configured to supply the gas mist between the first sheet and the second sheet, thereby contacting the gas mist to the eyes or the face of the human living organism, and an internal pressure of the gas mist storage is higher than that of the liquid storage such that the liquid is taken up from the liquid storage toward the gas mist storage, the gas mist generating device further comprises an upper plate and a lower plate apart from each other in the gas mist storage, each having pores therein so as to refine the gas mist; and a diameter of the pore of the upper plate is smaller than that of the lower plate, and the pores of the upper plate are placed out of alignment with those of the lower plate, the gas mist generating device further comprises a baffle connected the liquid suction pipe, a lower end of the baffle facing a front end of the nozzle and the liquid suction pipe so that the liquid stored in the liquid storage is adapted to collide with the lower end of the baffle to pulverize and dissolve the liquid with the gas from the gas supply device to generate the gas mist in the gas mist generating device, and the mask main frame further comprises a third sheet arranged at an opposite side of the second sheet relative to the first sheet and having opening at one part thereof such that a heating member moves in and removes from a space between the second sheet and the third sheet.

2. A gas mist mask device as set forth in claim 1, wherein the mask member has a shape of an eye mask.

3. A gas mist mask device as set forth in claim 1, wherein the mask member has a shape of a face mask.

4. A gas mist mask device as set forth in claim 1, wherein the gas supply device is a gas bomb of a cartridge system.

5. A gas mist mask device as set forth in claim 1, wherein the gas supply device has at least one of a gas supplying time setting part, a gas supplying pressure adjusting part, and a gas mixing ratio setting part.

6. A gas mist mask device as set forth in claim 1, wherein the gas mist generating device supplies the gas mist into a plurality of mask members.

7. A gas mist mask device as set forth in claim 1, wherein the liquid includes at least one of water, ionic water, ozone water, physiological salt solution, purified water and sterilized and purified water.

8. A gas mist mask device as set forth in claim 7, wherein the liquid further includes at least one of menthol, vitamin E, vitamin C derivative, retinol, anesthetic, cyclodextrin, photocatalyst, complex of photocatalyst and apatite, hyaluronic acid, coenzyme Q10, seed oil, propolith, silica, povidone-iodine, anti-allergic agent, anti-inflammatory agent, anti-febrile, anti-fungus agent, anti-influenza virus, influenza vaccine, steroid agent, anti-cancer substance, and anti-hypertensive agent.

9. A gas mist mask device as set forth in claim 1, wherein a grain size of the gas mist supplied from the gas mist generating device into the mask member is smaller than 10 μm.

10. A gas mist mask device as set forth in claim 1, wherein the gas mist generating device is shaped in a convex dome having a curved face toward an upper part and is provided with a gas mist discharge portion at a top of the dome for discharging the gas mist.

11. A gas mist mask device as set forth in claim 1, wherein the gas mist storage is provided with a gas supply port for directly supplying the gas from the gas supply device.

12. A gas mist mask device as set forth in claim 10, wherein the gas mist generating device has a gas mist supply pipe connected to the gas mist discharge portion for supplying the gas mist into the mask member, and the gas mist supply pipe has a filter to remove liquid drops attached to an inside thereof.

13. A gas mist mask device as set forth in claim 12, wherein at least one part of the gas mist supply pipe is composed of a cornice shaped pipe.

14. A gas mist mask device as set forth in claim 13, wherein the gas mist supply pipe is provided with a check valve.

15. A gas mist mask device as set forth in claim 11, wherein the mask member has a gas mist supply port for introducing the gas mist supplied from the gas mist generating device into a cover device, and the gas mist supply port has a check valve inside thereof.

16. A gas mist mask device as set forth in claim 1, wherein the heating member has an oxidation heating substance therein.

* * * * *